(12) United States Patent
Nichols et al.

(10) Patent No.: US 7,178,671 B2
(45) Date of Patent: Feb. 20, 2007

(54) PACKAGE

(75) Inventors: Ann M. Nichols, Appleton, WI (US); Scott R. Martin, Appleton, WI (US); James D. McManus, Appleton, WI (US); Kami L. Bechyne, Appleton, WI (US); Heather A. Sorebo, Appleton, WI (US); Mary Lou McDaniel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 105 days.

(21) Appl. No.: 10/010,934

(22) Filed: Nov. 13, 2001

(65) Prior Publication Data

US 2002/0060167 A1 May 23, 2002

Related U.S. Application Data

(63) Continuation-in-part of application No. 09/713,496, filed on Nov. 15, 2000, now abandoned.

(51) Int. Cl.
*B65D 85/00* (2006.01)

(52) U.S. Cl. .................. 206/438; 206/440; 206/494

(58) Field of Classification Search ............ 116/205; 206/440, 449, 451, 459.5, 471, 494, 499, 206/812, 204, 526; 229/81, 226, 228, 240, 229/243, 244; 383/2, 86, 87
See application file for complete search history.

(56) References Cited

U.S. PATENT DOCUMENTS

| 900,751 | A | 10/1908 | Lockwood |
|---|---|---|---|
| 1,671,825 | A | 5/1928 | Johnson |
| 1,750,375 | A | 3/1930 | Vinciguera |
| 2,305,402 | A | 12/1942 | Avery et al. |
| 2,573,309 | A | 10/1951 | Chipkevich |
| 2,603,266 | A | 7/1952 | Carroll |
| 2,750,033 | A | 6/1956 | Pickens |
| 2,870,955 | A | 1/1959 | Brady et al. |
| 3,062,371 | A | 11/1962 | Patience |
| 3,070,280 | A | 12/1962 | Richmond |

(Continued)

FOREIGN PATENT DOCUMENTS

| CA | 2025856 | 3/1991 |
|---|---|---|

(Continued)

OTHER PUBLICATIONS

PCT/US01/30964 International Search Report from the European Patent Office dated May 8, 2002.

(Continued)

*Primary Examiner*—Mickey Yu
*Assistant Examiner*—Jerrold Johnson
(74) *Attorney, Agent, or Firm*—Senniger Powers

(57) ABSTRACT

A package including at least one absorbent article and packaging. The packaging includes a flexible pocket having a hollow interior, an opening extending into the interior, a flap for covering the opening, and an adhesive closure positioned on the flap for releasably holding the flap in the closed position. The closure is spaced from a distal edge of the flap to permit a portion of the flap to be grasped and separated from the pocket without releasing the closure.

19 Claims, 15 Drawing Sheets

U.S. PATENT DOCUMENTS

| | | | |
|---|---|---|---|
| 3,160,273 A | 12/1964 | Reuther et al. | |
| 3,310,225 A | 3/1967 | Hoblit | |
| 3,314,464 A | 4/1967 | Veilleux | |
| 3,320,863 A | 5/1967 | Ells et al. | |
| 3,338,019 A | 8/1967 | Trewella et al. | |
| 3,405,861 A | 10/1968 | Bush | |
| 3,420,433 A | 1/1969 | Bostwick | |
| 3,557,853 A | 1/1971 | Jones | |
| 3,670,876 A | 6/1972 | Davis | |
| 3,674,195 A | 7/1972 | Stone | |
| 3,730,338 A | 5/1973 | Cheskey | |
| 3,735,918 A * | 5/1973 | Tundermann | 383/32 |
| 3,858,790 A | 1/1975 | Humphrey | |
| 3,982,687 A | 9/1976 | Auer et al. | |
| 3,990,872 A | 11/1976 | Cullen | |
| 4,073,950 A | 2/1978 | Hansen et al. | |
| 4,131,195 A | 12/1978 | Worrell | |
| 4,192,420 A | 3/1980 | Worrell, Sr. et al. | |
| 4,276,982 A | 7/1981 | Sibrava et al. | |
| 4,286,639 A | 9/1981 | Murphy | |
| 4,441,613 A | 4/1984 | Hain et al. | |
| 4,460,088 A | 7/1984 | Rugenstein et al. | |
| 4,502,599 A * | 3/1985 | Perecman | 206/554 |
| 4,546,029 A | 10/1985 | Cancio et al. | |
| 4,550,855 A | 11/1985 | Harrison | |
| 4,556,146 A | 12/1985 | Swanson et al. | |
| 4,679,693 A | 7/1987 | Forman | |
| 4,700,841 A | 10/1987 | Padgett, Jr. et al. | |
| 4,713,839 A | 12/1987 | Peppiatt | |
| 4,739,879 A | 4/1988 | Nakamura | |
| 4,743,245 A | 5/1988 | Lassen et al. | |
| 4,785,940 A | 11/1988 | Wilson | |
| 4,786,190 A | 11/1988 | Van Erden et al. | |
| 4,834,241 A | 5/1989 | Southern | |
| 4,838,327 A | 6/1989 | Ambler et al. | |
| 4,917,675 A | 4/1990 | Taylor et al. | |
| 4,934,535 A | 6/1990 | Muckenfuhs et al. | |
| 4,948,028 A | 8/1990 | Vollowitz | |
| 4,964,859 A | 10/1990 | Feldman | |
| 4,966,286 A | 10/1990 | Muckenfuhs | |
| 4,979,613 A | 12/1990 | McLaughlin et al. | |
| 5,046,620 A | 9/1991 | Barabino | |
| 5,048,687 A | 9/1991 | Suzuki et al. | |
| 5,050,742 A | 9/1991 | Muckenfuhs | |
| 5,054,619 A | 10/1991 | Muckenfuhs | |
| 5,065,868 A | 11/1991 | Cornelissen et al. | |
| 5,076,465 A | 12/1991 | Lawson | |
| 5,082,112 A | 1/1992 | Dunklee | |
| 5,242,057 A | 9/1993 | Cook et al. | |
| 5,261,531 A | 11/1993 | Nieves | |
| 5,358,171 A * | 10/1994 | Focke | 229/87.05 |
| 5,391,136 A | 2/1995 | Makowka | |
| 5,413,568 A | 5/1995 | Roach et al. | |
| D360,577 S | 7/1995 | van Loo | |
| 5,476,323 A | 12/1995 | Gold | |
| D365,981 S | 1/1996 | Sullivan | |
| 5,560,798 A | 10/1996 | Brusky | |
| 5,569,230 A | 10/1996 | Fisher et al. | |
| 5,579,916 A | 12/1996 | Manko | |
| 5,639,523 A | 6/1997 | Ellis | |
| 5,655,842 A | 8/1997 | Hagino | |
| 5,730,294 A | 3/1998 | Blosser et al. | |
| 5,778,954 A | 7/1998 | Sullivan et al. | |
| 5,884,771 A | 3/1999 | McCormick | |
| 5,941,641 A * | 8/1999 | Kinigakis et al. | 383/86 |
| 5,951,505 A | 9/1999 | Gilman et al. | |
| 5,954,201 A | 9/1999 | Finch et al. | |
| 5,971,153 A | 10/1999 | Bauer et al. | |
| 5,996,797 A | 12/1999 | Flaig | |
| 6,015,045 A * | 1/2000 | Joseph et al. | 206/494 |
| 6,039,175 A | 3/2000 | Wright | |
| 6,041,928 A | 3/2000 | Jousinen et al. | |
| 6,059,100 A | 5/2000 | Jones | |
| 6,115,997 A | 9/2000 | Burrow et al. | |
| 6,126,009 A | 10/2000 | Shiffler et al. | |
| 6,168,022 B1 | 1/2001 | Ward et al. | |
| 6,257,473 B1 | 7/2001 | Ringelstetter | |
| 6,338,572 B1 | 1/2002 | Schneck | |
| 2002/0063076 A1 | 5/2002 | Kolterjohn et al. | |
| 2002/0064322 A1 | 5/2002 | May | |

FOREIGN PATENT DOCUMENTS

| | | |
|---|---|---|
| CA | 2 109 782 | 5/1995 |
| DE | 83 19 608 | 12/1984 |
| DE | 39 23 839 A1 | 10/1990 |
| EP | 0 419 770 A1 | 4/1991 |
| EP | 1 043 004 A2 | 10/2000 |
| FR | 1 482 194 | 4/1966 |
| WO | WO 94/00362 | 1/1994 |
| WO | WO 98/18682 | 5/1998 |
| WO | WO 98/57610 | 12/1998 |
| WO | WO 99/26576 | 6/1999 |
| WO | WO 02/08087 A2 | 1/2002 |

OTHER PUBLICATIONS

PCT/US01/44975 International Search Report from the European Patent Office dated May 8, 2002.

* cited by examiner

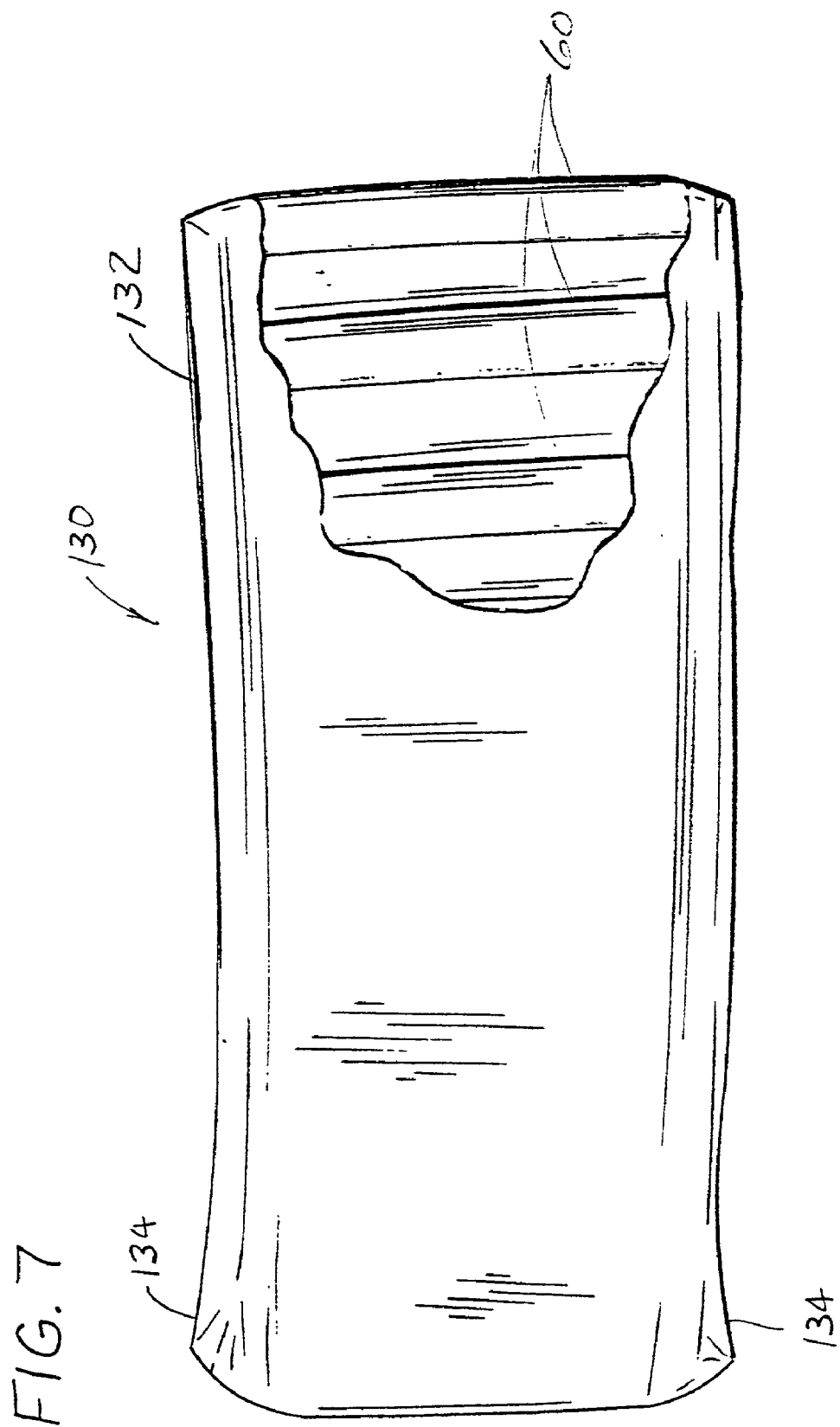

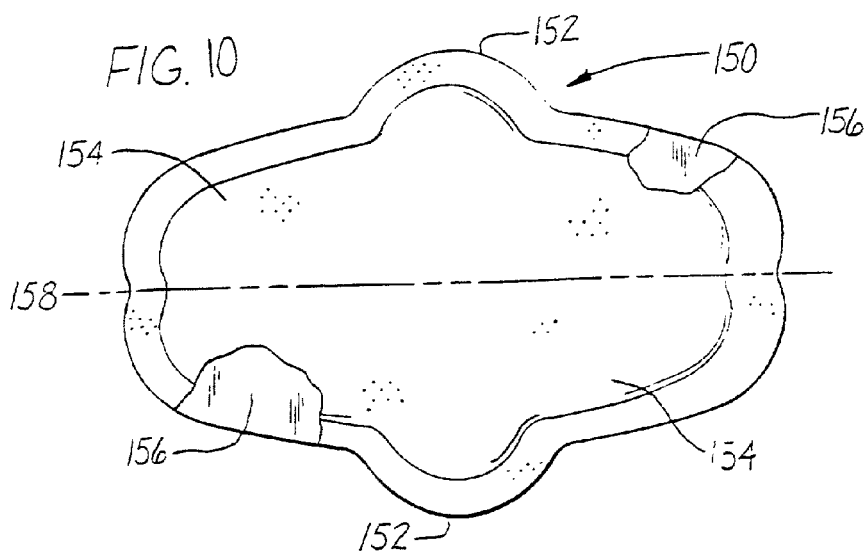
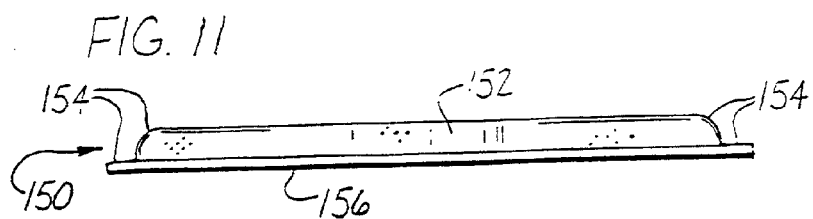
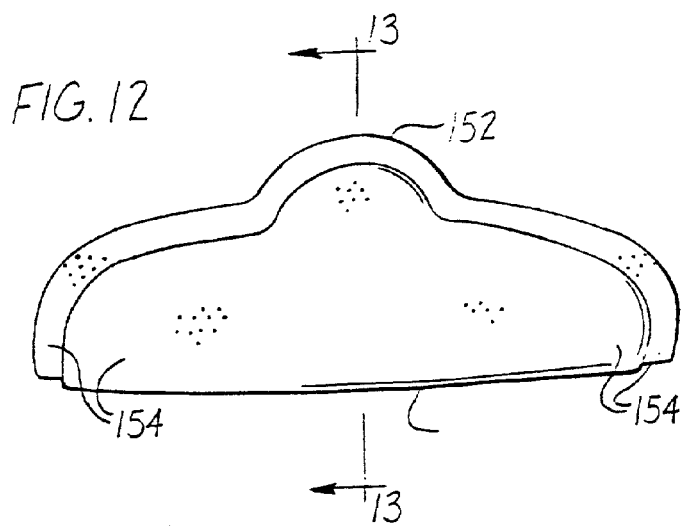
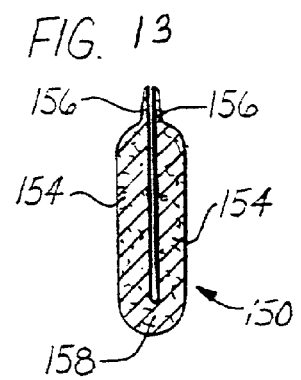

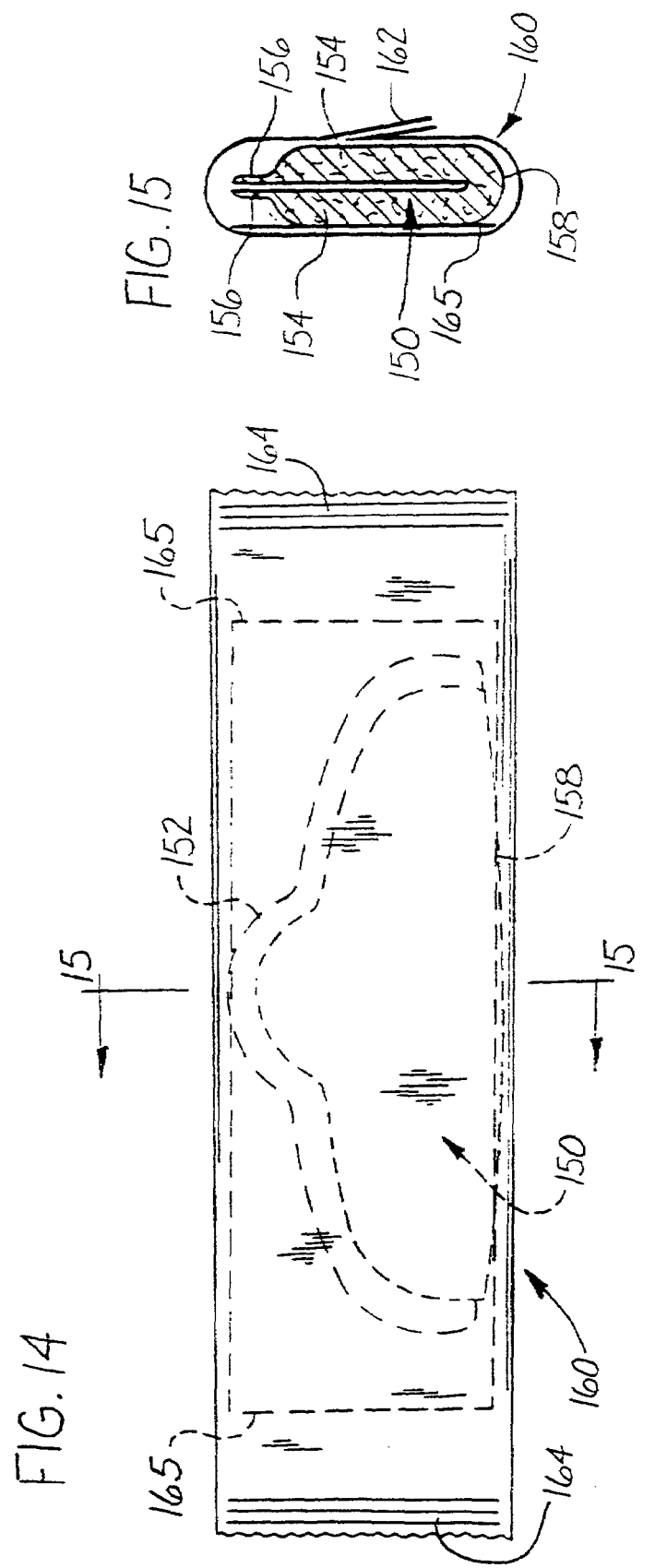

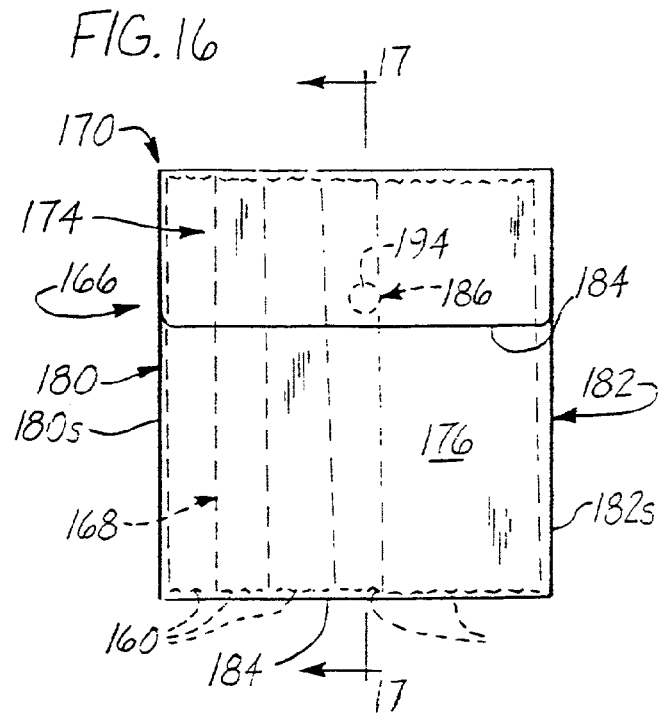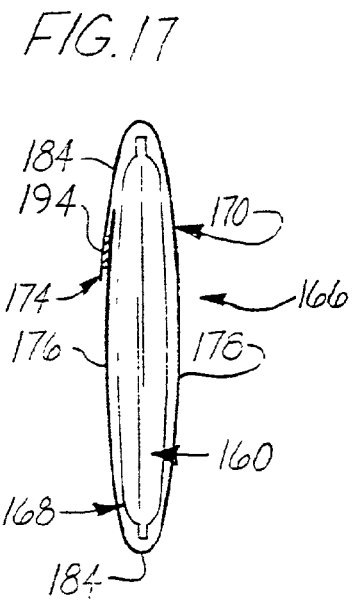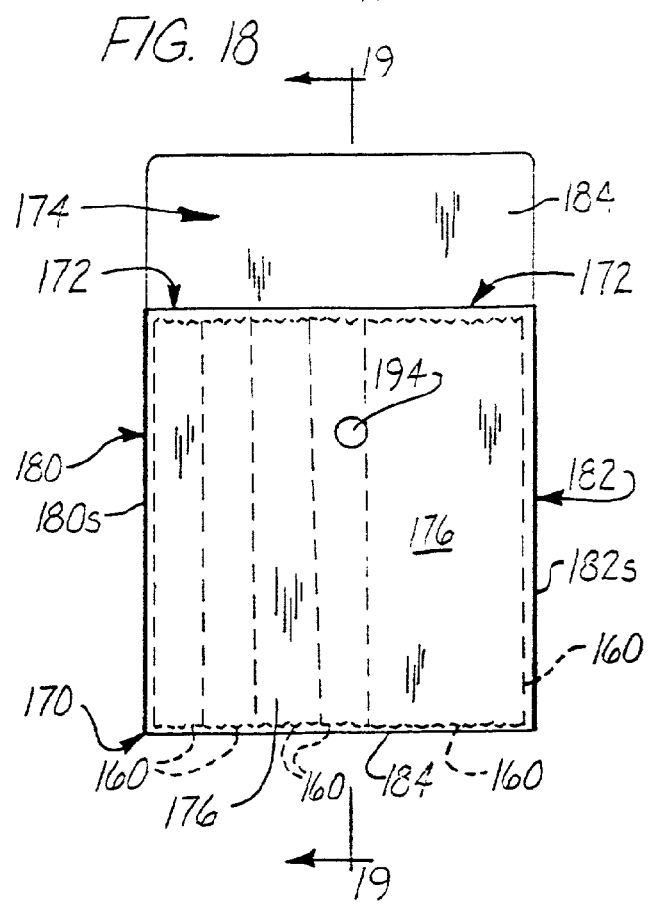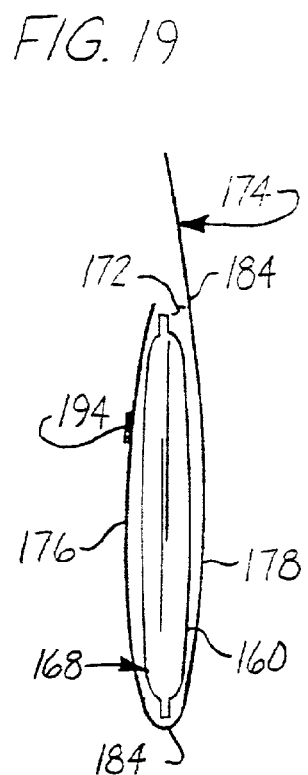

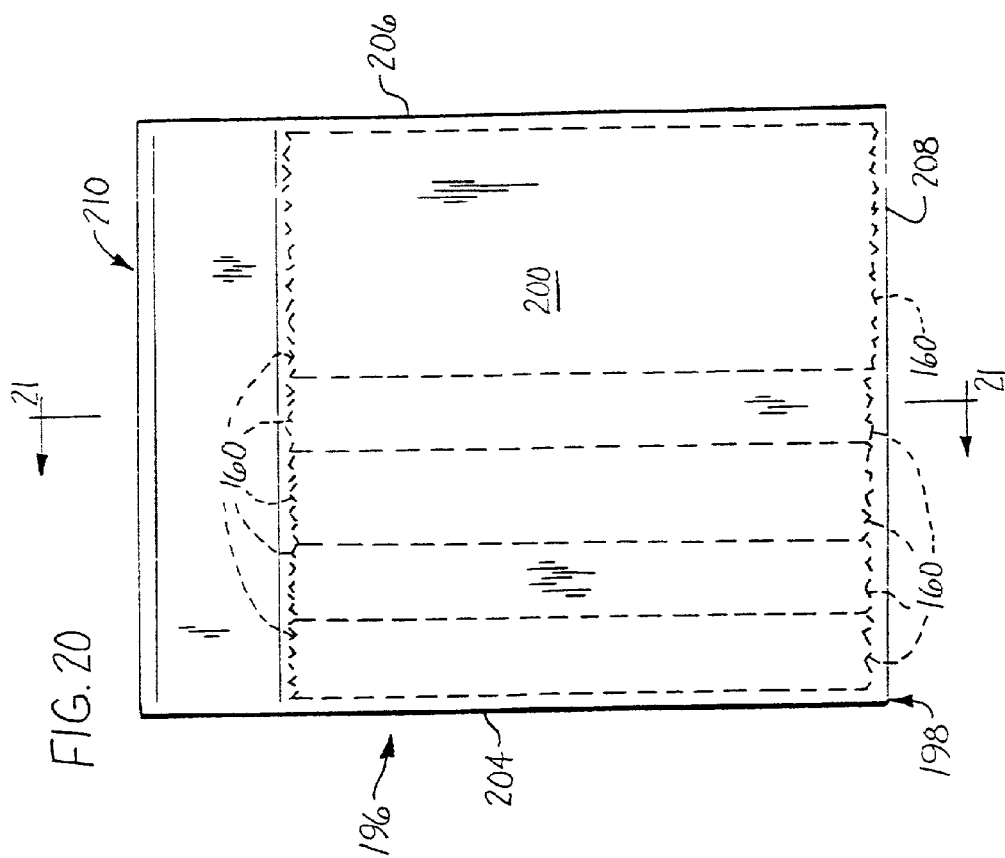

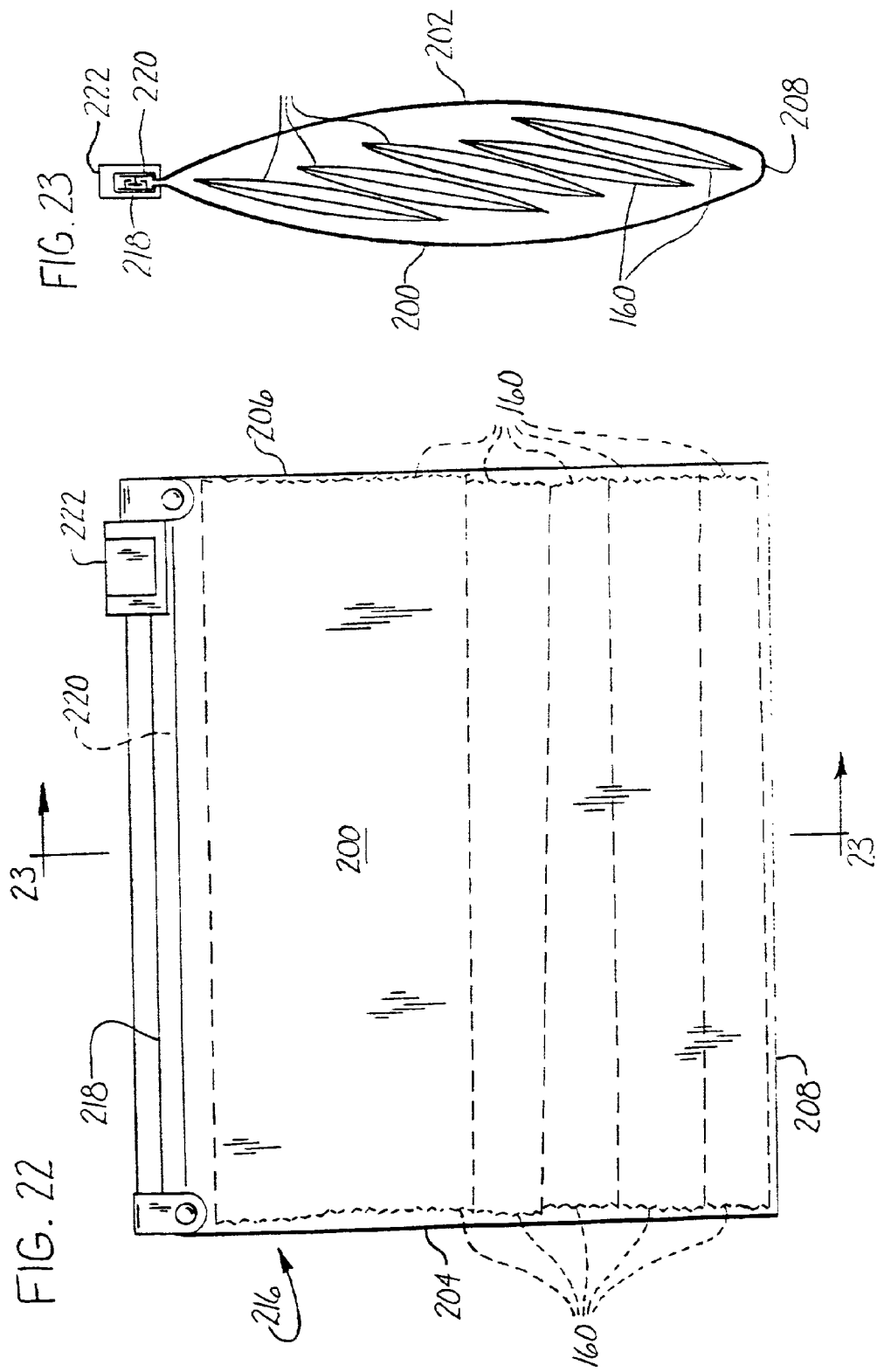

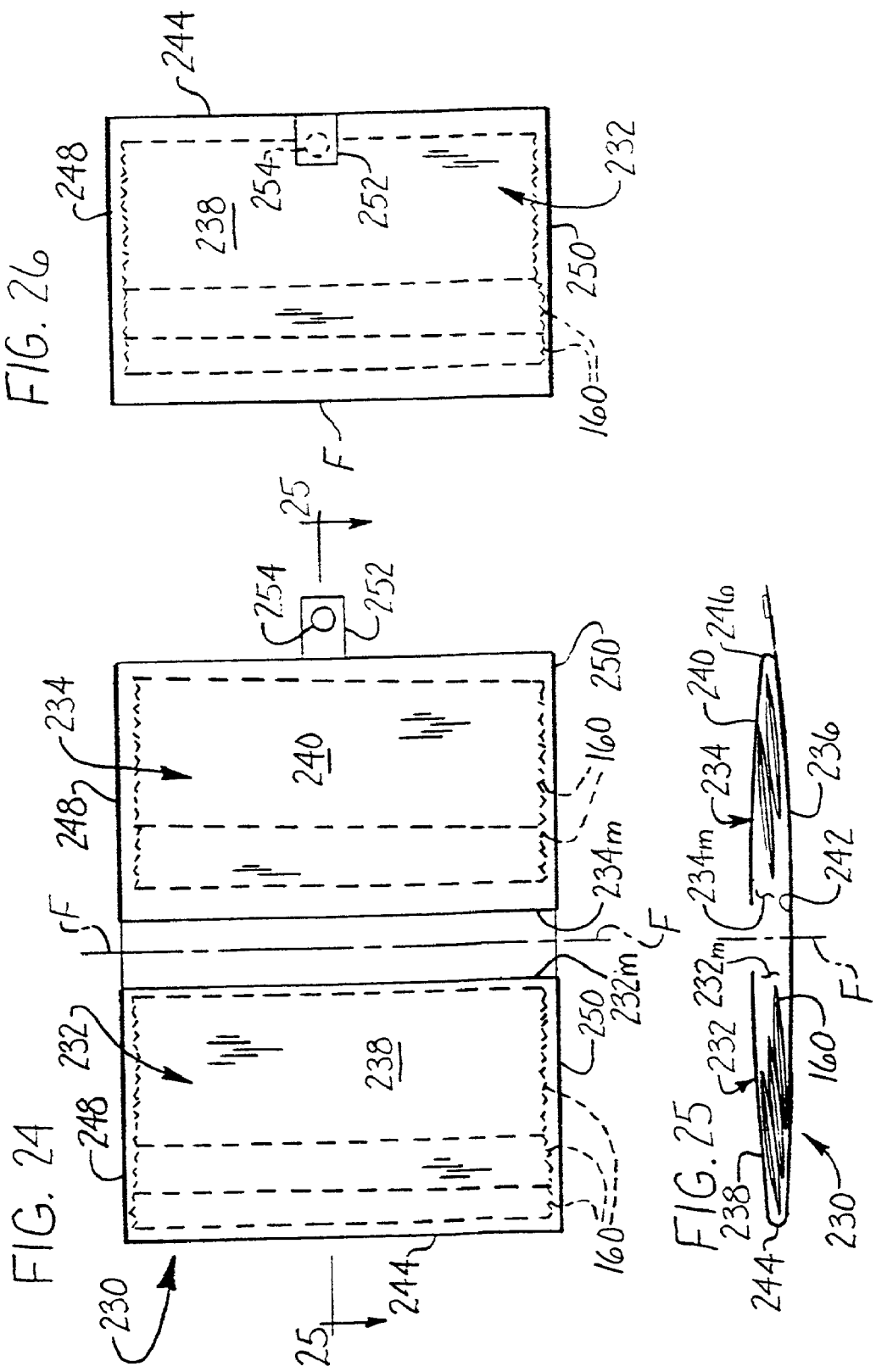

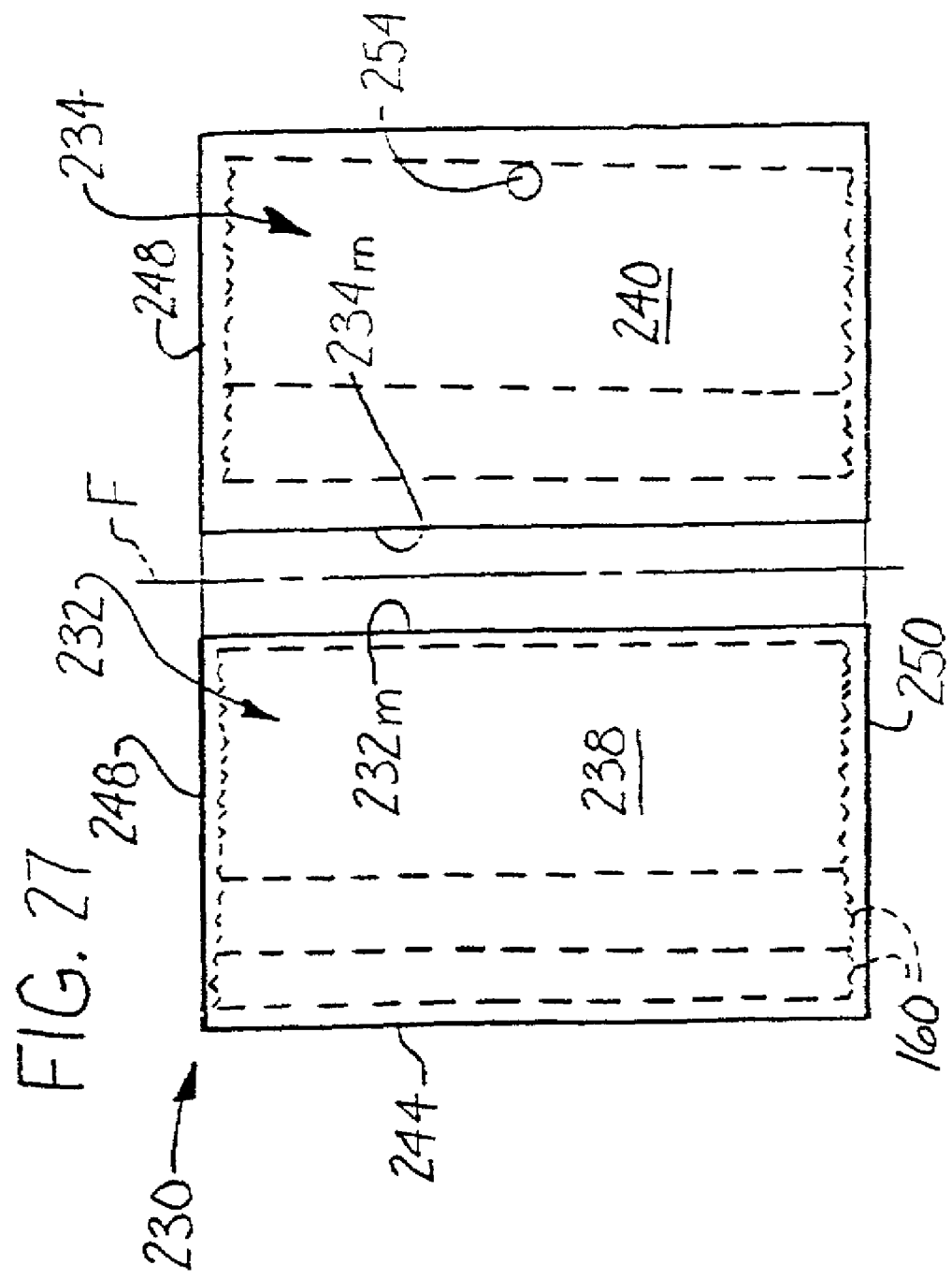

PACKAGE

CROSS-REFERENCE TO RELATED APPLICATION

This is a continuation-in-part of U.S. patent application Ser. No. 09/713,496, filed Nov. 15, 2000, entitled, "PACKAGE", now abandoned, which is hereby incorporated by reference in its entirety.

BACKGROUND OF THE INVENTION

The present invention relates generally to a package, and more particularly to packaging for absorbent articles having a closure and a flap adapted to be grasped without releasing the closure.

Absorbent articles such as panty liners, feminine napkins and tampons are frequently carried about in purses, backpacks and briefcases until needed. Typically, the articles are put in these containers loose. Unfortunately, these containers do not always provide a hygienic environment for the articles, and thus the articles can become dirty and/or damaged. Further, the articles can become scattered about in the containers so they are difficult to find when needed.

In the past, specifically designed pouches have been distributed for holding several absorbent articles at a time. These pouches reduce contact between the articles and potentially non-hygienic environments, and make the articles easier to find when needed. The pouches are made from durable materials such as heavy vinyl so they can be reused, but reuse necessitates the pouches be refilled from time to time. Further, the pouches frequently become non-hygienic after extended use, requiring them to be cleaned or discarded and replaced.

To avoid these problems, some persons use clear plastic sandwich bags to hold the articles. These bags usually maintain a hygienic environment for the articles and make the articles easier to find when needed. Although the bags must be filled from time to time, they are readily disposable and replaceable thereby reducing some of the concerns and inconveniences caused by extended use. However, because the bags are transparent, they permit the contents of the bags to be viewed. Some users desire more discreet packaging. Thus, there is a need for a discreet, disposable and economical recloseable package for holding several articles at a time.

One type of packaging which meets the previously mentioned need is described in a co-assigned U.S. Patent Application, entitled "Package for Absorbent Articles", filed Nov. 15, 2000, and identified as KCC 4728, which is hereby incorporated by reference in its entirety. This packaging includes a pocket for holding the articles and a opening for withdrawing articles from the pocket when needed. Further, the package includes a flap for selectively covering the opening. The flap has an adhesive closure for holding the flap against the pocket when covering the opening. It has been noted that the adhesive closure and/or flap can be difficult to grasp when separating the flap from the pocket to uncover the opening when articles are needed. Thus, there is a need for packaging having a flap which can easily be grasped when opening and closing the packaging.

SUMMARY OF THE INVENTION

Briefly, apparatus of this invention is a package comprising at least one absorbent article and packaging. The packaging includes a flexible pocket having a hollow interior sized and shaped for receiving the absorbent article and an opening extending into the hollow interior of the pocket sized and shaped for permitting the article to be withdrawn from the hollow interior of the pocket. In addition, the packaging includes a flap attached to the pocket adapted for covering the opening to retain the absorbent article in the hollow interior of the pocket. The flap is selectably moveable between an open position in which the opening is generally unobstructed by the flap to permit the article to be withdrawn through the opening and a closed position in which the flap covers the opening and an exterior area of the pocket to retain the article in the pocket and to prevent the article from passing through the opening. Further, the packaging includes an adhesive closure positioned on the flap for releasably holding the flap in the closed position. The closure is spaced from a distal edge of the flap to permit a portion of the flap to be grasped and separated from the pocket without releasing the closure.

Other objects and features of the present invention will be in part apparent and in part pointed out hereinafter.

BRIEF DESCRIPTION OF THE DRAWINGS

FIG. 7 is a front elevation of a master package of a second embodiment of the present invention with a portion broken away to show utility packages therein;

FIG. 10 is a plan view of an interlabial pad such as may be packaged in accordance with this invention, partly broken away to show detail;

FIG. 11 is a edge view of the interlabial pad;

FIG. 12 is a plan view showing the pad folded;

FIG. 13 is a section taken in the plane of line 13—13 of FIG. 12;

FIG. 14 is a front elevation of hygienic packaging containing the folded pad;

FIG. 15 is a section taken in the plane of line 15—15 of FIG. 14;

FIG. 16 is a front elevation of a package of a fourth embodiment of the present invention in a closed condition, the packaged pads therein shown in dashed lines;

FIG. 17 is a section taken in the plane of line 17—17 of FIG. 16;

FIG. 18 is a front elevation of the package of FIG. 16 in an opened condition;

FIG. 19 is a section taken in the plane of line 18—18 of FIG. 18;

FIG. 20 is a front elevation of a package of a fifth embodiment of the present invention, the packaged pads therein shown in dashed lines;

FIG. 21 is a section taken in the plane of line 21—21 of FIG. 20;

FIG. 22 is a front elevation of a package of a sixth embodiment of the present invention, the packaged pads therein shown in dashed lines;

FIG. 23 is a section taken in the plane of line 23—23 of FIG. 22;

FIG. 24 is a front elevation of a package of a seventh embodiment of the present invention in an opened condition, the packaged pads therein shown in dashed lines;

FIG. 25 is a section taken in the plane of line 25—25 of FIG. 24;

FIG. 26 is a front elevation of the package of FIG. 24 in an opened condition; and FIG. 27 is a front elevation of a package of a eighth embodiment of the present invention in an opened condition, the packaged pads therein shown in dashed lines.

Corresponding reference characters indicate corresponding parts throughout the several views of the drawings.

DETAILED DESCRIPTION OF THE PREFERRED EMBODIMENT

Figure 1:
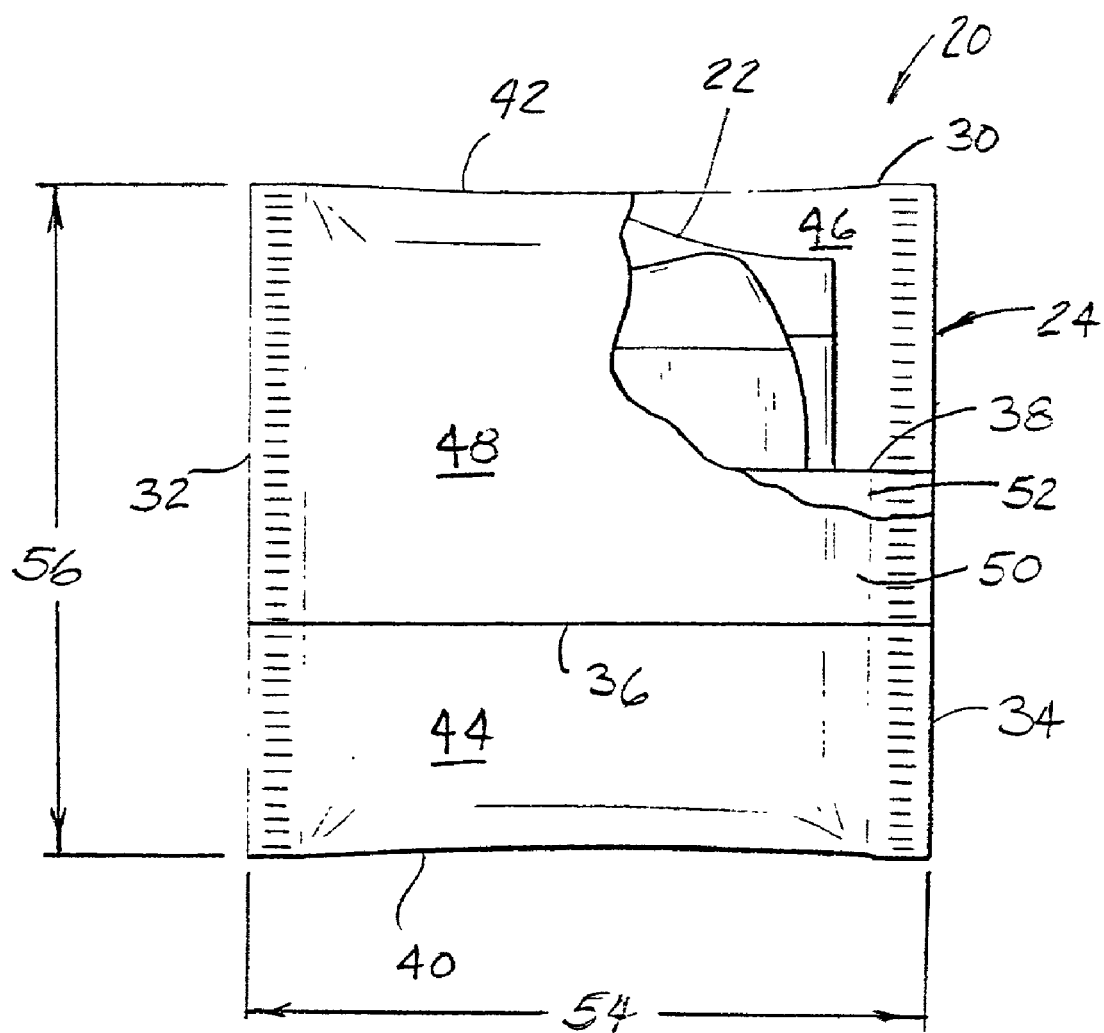
FIG. 1 is a front elevation of a prior art panty liner surrounded by a removable wrapper.

Referring now to the drawings and in particular to FIG. 1, a conventional individually wrapped absorbent article is designated in its entirety by the reference numeral 20. Although the absorbent article 20 shown in FIG. 1 is a panty liner 22 surrounded by a wrapper, generally designated by 24, those skilled in the art will appreciate that the present invention may be applied to other absorbent articles 20 such as feminine napkins, tampons, interlabial pads, other feminine care products, adult care products, child care products and infant care products. Further, those skilled in the art will appreciate that although the illustrated articles 20 are individually wrapped, the articles may be unwrapped without departing from the scope of the present invention.

The panty liner 22 shown in FIG. 1 is folded twice in a conventional manner to present a generally flat and generally rectangular article. Although the folded panty liner 22 may have other sizes without departing from the scope of the present invention, in one embodiment the folded liner has a width of about 50 millimeters, a length of about 70 millimeters and a thickness of about 5 millimeters. It is also envisioned that the panty liner 22 may be unfolded and/or non-rectangular without departing from the scope of the present invention.

Although the wrapper 24 may be made in other ways without departing from the scope of the present invention, in one embodiment the wrapper includes a rectangular sheet 30 having opposing side edges 32, 34 and opposite end edges 36, 38. A first fold 40 in the sheet 30 extending between the side edges 32, 34 forms a bottom of the wrapper 24, and a second fold 42 in the sheet extending between the side edges generally parallel to and above the first fold forms a top of the wrapper. The first fold 40 separates a middle portion 44 of the wrapper 24 from a back portion 46, and the second fold 42 separates the middle portion from a front portion 48 of the wrapper. The side edges 32, 34 of the middle portion 44 are joined to the back portion 46, and the side edges of the forward portion 48 are joined to the middle portion to form opposing sides of the wrapper. A margin 50 of the sheet 30 adjacent the end edge 36 overlaps a margin 52 of the sheet adjacent the end edge 38. It is envisioned that it may be desirable to join the side edges 32, 34 of the forward portion 48 to the back portion 46.

Although the side edges 32, 34 of the rectangular sheet 30 may be joined in other ways (such as with adhesives or by heat sealing) without departing from the scope of the present invention, in one embodiment the side edge margins are joined by conventional mechanical fastening means as shown. Although the wrapped article 20 may have other sizes without departing from the scope of the present invention, in one embodiment the article has a width 54 of about 75 millimeters, a length 56 of about 75 millimeters and a thickness 58 (FIG. 4) of about 5 millimeters. Further, although the dimensions of the article 20 may vary from article to article without departing from the scope of the present invention, in one embodiment the dimensions are generally uniform. In addition, the dimensions may vary within a given article or they may be invariant without departing from the scope of the present invention. Although the wrapper 24 may be made of other materials without departing from the scope of the present invention, in one embodiment the wrapper is made from low density polyethylene sheet material having a thickness of about 38 microns. It is further envisioned that the wrapper 24 may have an adhesive or other closure (not shown) without departing from the scope of the present invention.

Figure 2:
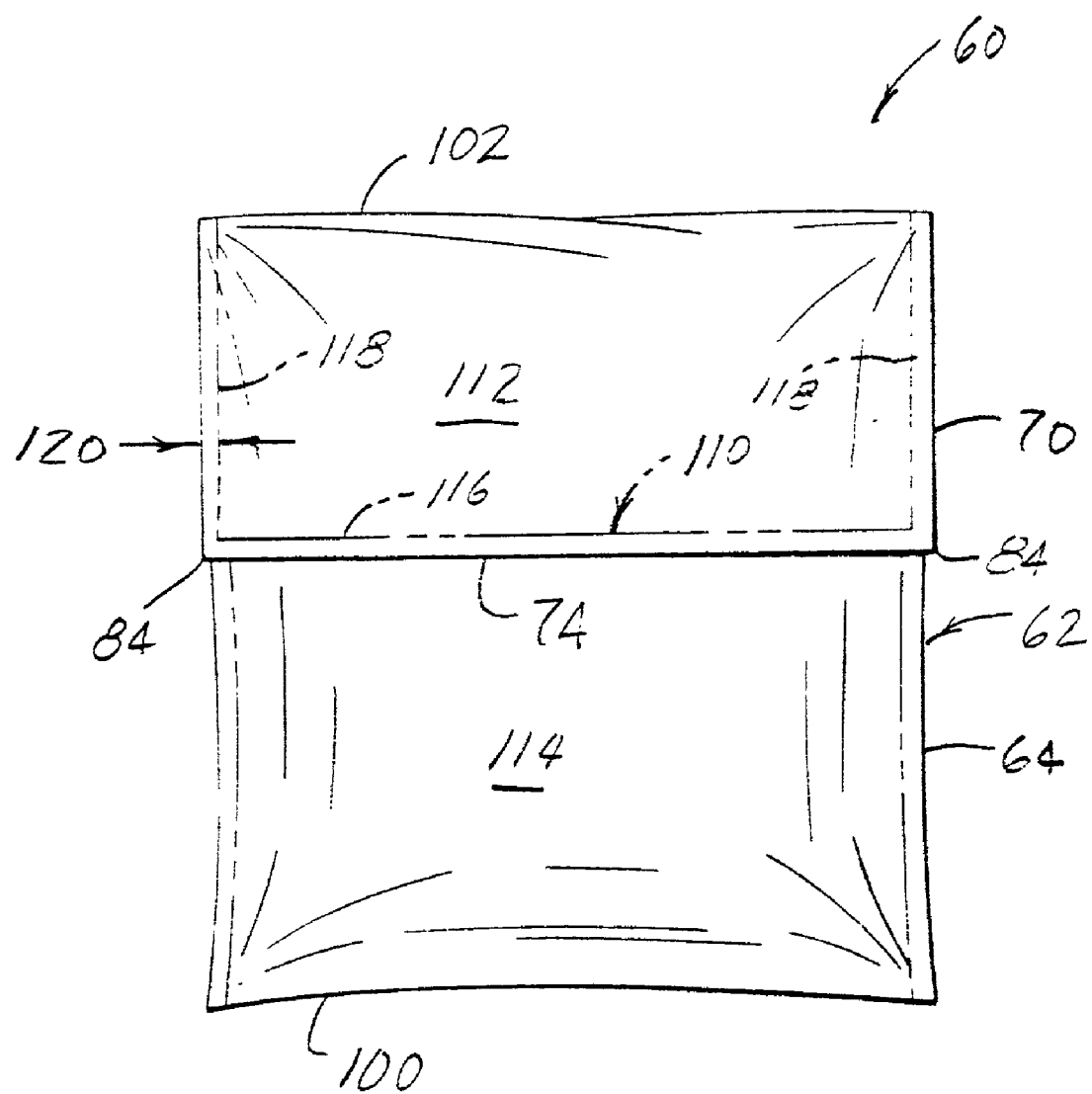
FIG. 2 is a front elevation of a utility package of the present invention showing a flap of the package in a closed position.
Figure 3:
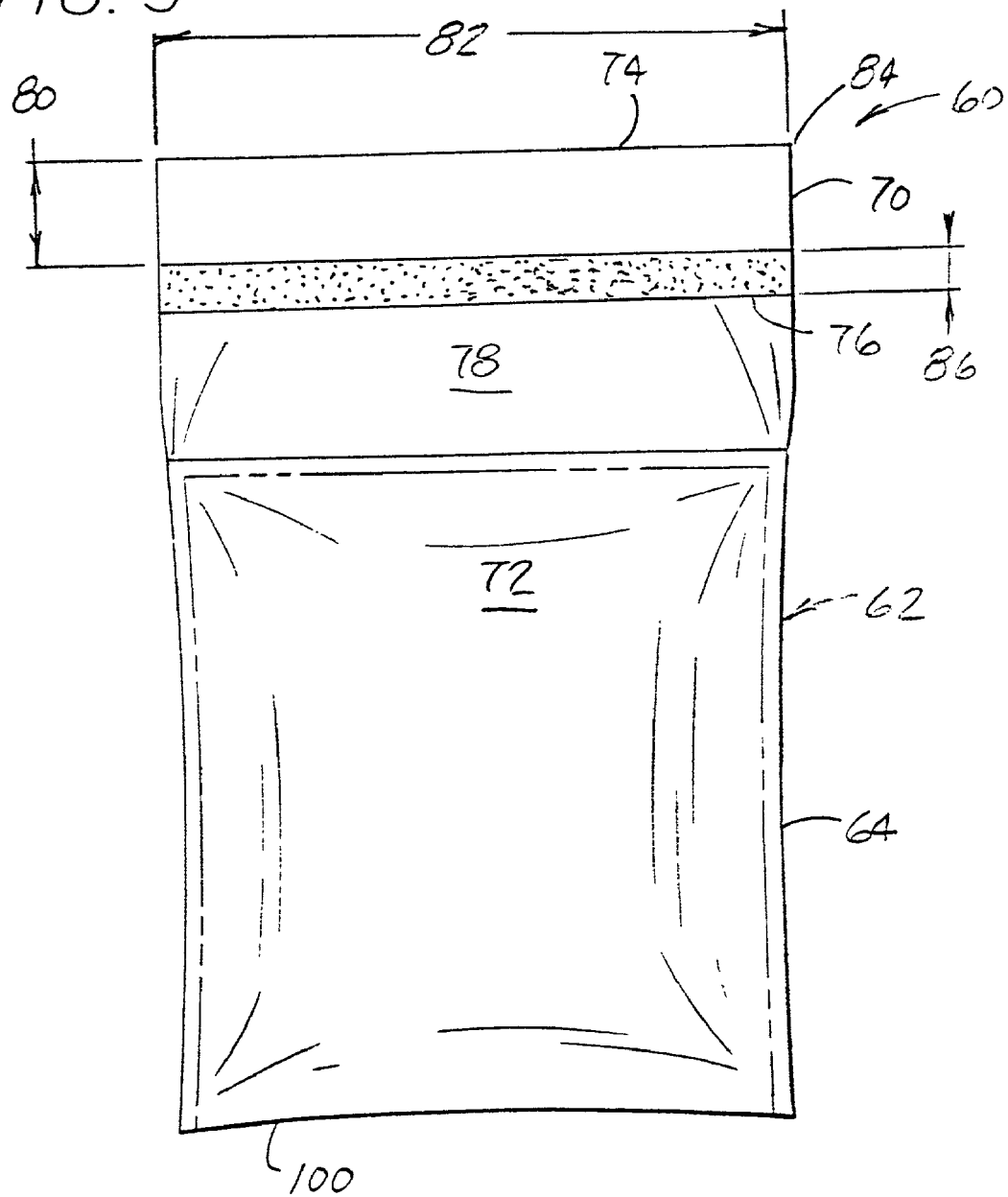
FIG. 3 is a front elevation of the utility package showing the flap in an open position.
Figure 4:
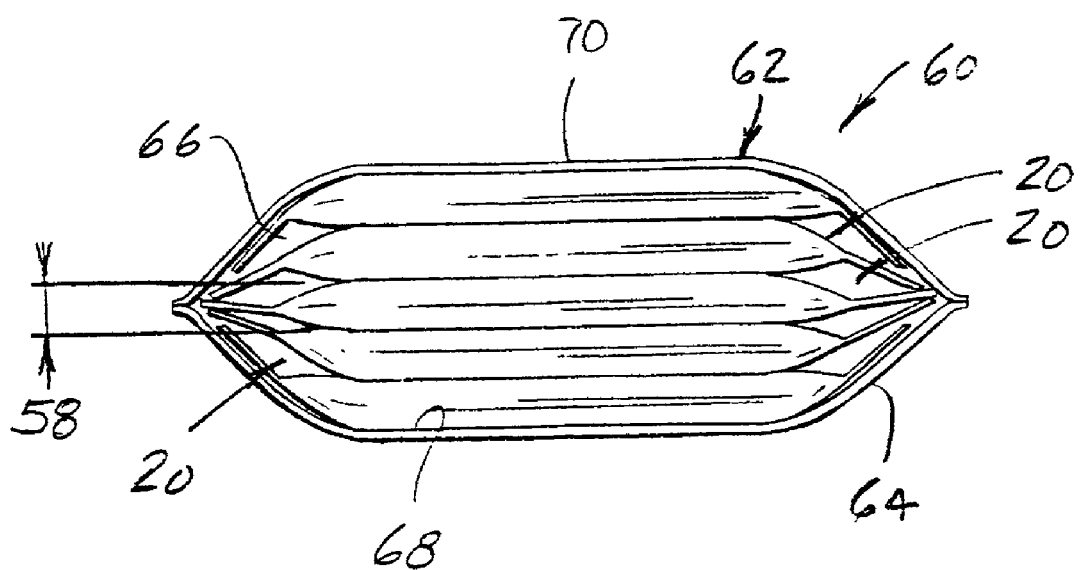
FIG. 4 is a top plan of the utility package showing the flap in the open position.

As illustrated in FIGS. 2–4, a utility package of the present invention is designated in its entirety by the reference numeral 60. The package 60 generally comprises a plurality of absorbent articles 20 (FIG. 4) and recloseable packaging, generally designated by 62. As previously mentioned, it is envisioned that the articles 20 may be folded or unfolded and individually wrapped or unwrapped without departing from the scope of the present invention. Although the articles 20 may be arranged in other ways without departing from the scope of the present invention, in one embodiment the articles are arranged in face-to-face relation in a stack as illustrated in FIG. 4. The package 60 includes a number of articles 20 which is selected for the convenience of an end user. For example, the package 60 may include less than about eight absorbent articles 20 to provide a supply of articles for about one week or less. It is envisioned that it may be desirable that the package 60 include about five absorbent articles 20 to provide a supply of articles for one conventional work week (i.e., five days).

The packaging 62 includes a flexible pocket 64. The pocket 64 has a hollow interior 66 sized and shaped for receiving the preselected number of absorbent articles 20 as shown in FIG. 4. An opening 68 extends into the hollow interior 66 of the pocket 64. The opening 68 is sized and shaped for permitting at least one of the plurality of articles 20 to be withdrawn from the hollow interior 66 of the pocket 64. Further, the packaging 62 includes a flap 70 attached to the pocket 64 adapted for covering the opening 68 to retain the plurality of articles 20 in the hollow interior 66 of the pocket 64. The flap 70 is selectably moveable between an open position as illustrated in FIG. 3 in which the opening 68 is generally unobstructed by the flap to permit at least one article 20 to be withdrawn through the opening and a closed position as shown in FIG. 2 in which the flap covers the opening and an exterior area 72 (FIG. 3) of the pocket 64 to retain the articles in the pocket and to prevent the articles from passing through the opening. As shown in FIG. 2, in its closed position the flap is overlapped with the portion of the exterior area 72 that it covers and is thus free from flush alignment with the pocket. In one embodiment, the flap 70 is substantially rectangular and has a substantially straight distal edge 74. However, those skilled in the art will appreciate that the flap 70 may have other shapes such as semi-circular or triangular without departing from the scope of the present invention.

As illustrated in FIG. 3, a closure 76 is positioned on an inner face 78 of the flap 70 for releasably holding the flap in the closed position. It is envisioned that the closure 76 may be positioned on the exterior area 72 of the pocket 64 instead of or in addition to being positioned on the flap 70. Preferably, the closure 76 permits the flap 70 to be positioned in a different location on the pocket 64 during successive closings when successive articles 20 are removed from the interior 66 of the pocket to permit the packaging 62 to conform to the remaining articles in the interior of the pocket. Although other closures 76 may be used without departing from the scope of the present invention, in one embodiment the closure is an adhesive material such as a conventional resealable hot melt adhesive or a resealable two sided tape for releasably holding the flap 70 in the closed position.

Although the closure 76 may be positioned at other locations without departing from the scope of the present invention, in one embodiment the closure is spaced from the distal edge 74 of the flap 70 to permit a free portion of the flap to be grasped and separated from the pocket 64 to grip the flap for releasing the closure. It is envisioned that it may be desirable that the closure 76 be spaced from the distal edge 74 of the flap 70 by a distance 80 of at least about 4 millimeters. It is further envisioned that it may be desirable that the distance 80 be about 16 millimeters.

Although the closure 76 may have other shapes without departing from the scope of the present invention, in one embodiment the closure is an elongate strip of adhesive material extending substantially parallel to the distal edge 74 of the packaging flap 70. In one embodiment, the strip of adhesive material is substantially continuous and uninterrupted along its entire length, but it is envisioned that other embodiments may have adhesive material which is discontinuous and/or interrupted along its length without departing from the scope of the present invention. In addition, it is envisioned that it may be desirable that the strip extend over substantially an entire width 82 of the flap 70 so the corners 84 of the flap are held in place near the pocket 64. Although the elongate strip may have other widths without departing from the scope of the present invention, in one embodiment the strip has a width 86 of less than about 20 millimeters and more than about 2 millimeters. It may be desirable that the width 86 of the strip be about 7 millimeters.

Figure 5:
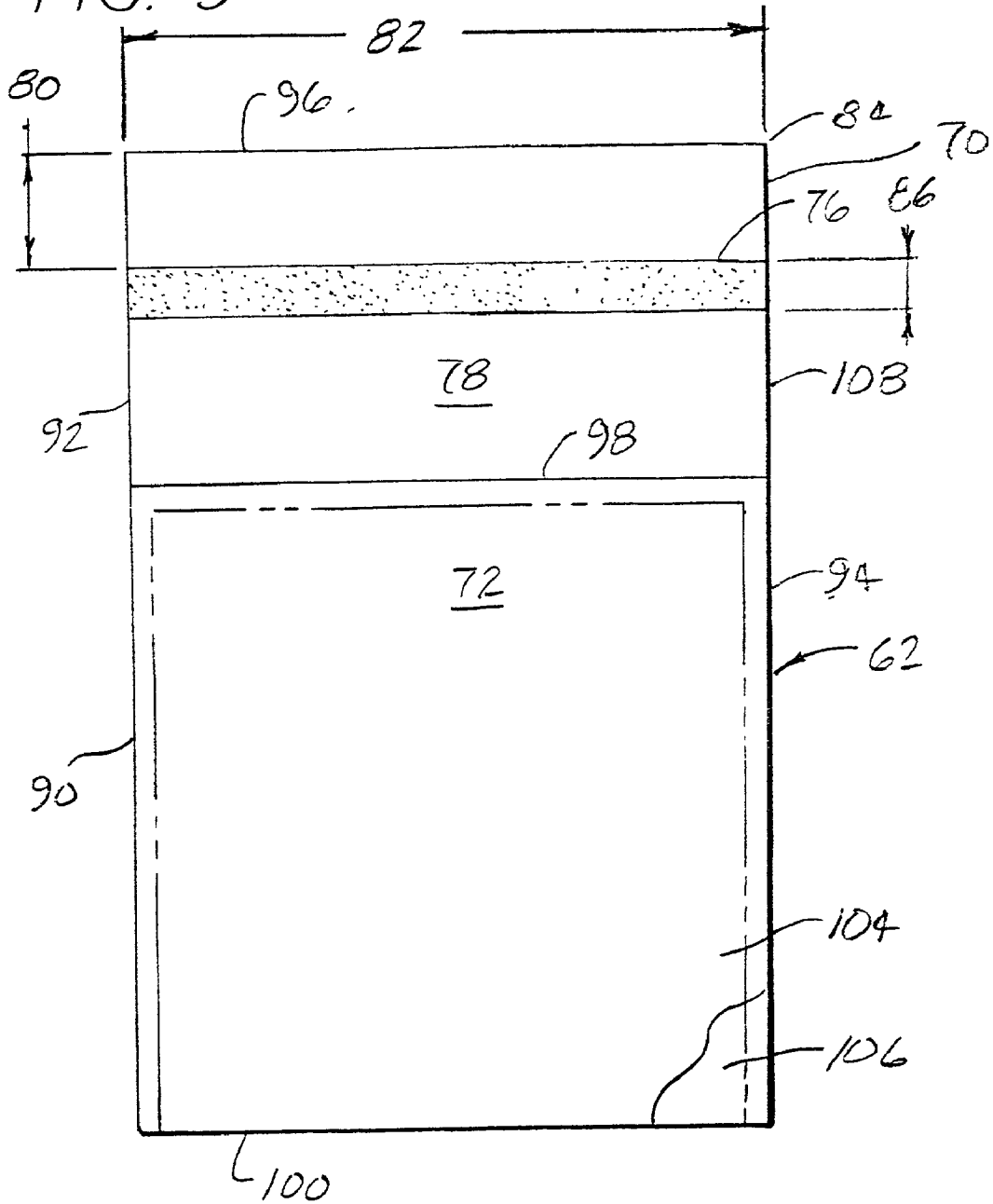
FIG. 5 is a front elevation of empty packaging of the utility package.

Although the packaging 62 may be made in other ways without departing from the scope of the present invention, in one embodiment illustrated in FIG. 5 the packaging comprises a rectangular sheet 90 having opposing side edges 92, 94 and opposite end edges 96, 98. A first fold 100 extending between the side edges 92, 94 forms a bottom of the packaging 62, and a second fold 102 (FIG. 2) extending between the side edges generally parallel to and above the first fold forms a top of the packaging. The first fold 100 separates a middle portion 104 of the packaging 62 from a back portion 106. The middle and back portions 104, 106, respectively, form the pocket 64 of the packaging 62. The second fold 102 separates the back portion 106 from a front portion 108 of the packaging 62. The front portion 108 of the packaging 62 forms the flap 70. Although the second fold 102 may be positioned in other locations without departing from the scope of the present invention, in one embodiment the second fold is positioned immediately adjacent the opening 68 and immediately adjacent an upper end of the front portion 108 (i.e., adjacent the edge 98 of the sheet 90). The middle portion 104 is joined with the corresponding back portion 106 along side edges 92, 94 to form opposing sides of the packaging 62. Although the middle and back portions 104, 106 may be joined in other ways (such as with adhesives or by mechanical fastening) without departing from the scope of the present invention, in one embodiment they are joined by conventional heat sealing. Although the packaging 62 may be made from other materials without departing from the scope of the present invention, in one embodiment the packaging is made from a heat sealable polymer sheet material such as a material containing about 80% polyethylene and about 20% other polyolefins having a thickness of about 45 microns available from Shanghai Zihua Enterprise Company, Limited of Shanghai, China. It is further envisioned that the packaging 62 may be made from coated paper, woven material, non-woven material, polyethylene, polypropylene, co-polymers, extruded polymer, thermo-formed materials, and/or cardboard without departing from the scope of the present invention. Although in one embodiment the pocket 64 is substantially free of gussets, in an alternate embodiment the sides of the pocket may include conventional gussets (not shown) to provide the packaging 62 with a substantially flat bottom.

Although the interior 66 of the packaging 62 defined by the flap 70 and the pocket 64 may have other sizes without departing from the scope of the present invention, it may be desirable that the interior have a volume when receiving the preselected number of articles 20 less than about twice the number of articles times a product of the article width 54, length 56 and thickness 58, and more than about one times the number of articles times the product of the article width, length and thickness. As previously mentioned, the number of articles 20 is selected for the convenience of an end user. For example, it is envisioned that it may be desirable that the package 60 include about five absorbent articles 20 to provide a supply of articles for one conventional work week (i.e., five days). Moreover, it may be desirable that the interior 66 have a width when the articles are removed and the pocket 64 is flattened as shown in FIG. 5 less than about twice the article width 54, and a width when receiving the preselected number of articles more than about one times the article width. In one embodiment, the width of the hollow interior 66 when the articles 20 are removed is about 1.2 times the article width. Likewise, it may be desirable that the interior 66 have a length when the articles are removed and the pocket 64 is flattened less than about twice the article length 56, and a length when receiving the preselected number of articles more than about one times the article length. In one embodiment, the length of the hollow interior 66 when the articles 20 are removed is about 1.2 times the article length 56. Further, in one embodiment the opening 68 has a width when the pocket 62 receives the articles 20 less than about two times the article width 54 and more than about one times the article width. It may be desirable that the opening width be about 1.2 times the article width 54. In one embodiment, the opening 68 has an area when the pocket receives the preselected number of articles 20 less than about twice the number of articles times a product of the article width 54 and thickness 58, and more than about one times the number of articles times the product of the article width and thickness.

As illustrated in FIG. 2, it may be desirable that the flap 70 and/or the pocket 64 include a visual indicator, generally designated by 110, for distinguishing the edge 74 of the flap from the pocket. The indicator 110 improves visual identification of the edge 74 of the flap 70 when grasping the flap to move it toward its open position. The visual indicator 110 comprises visually contrasting surface treatments on the flap 70 and the pocket 64. Although other visually contrasting surface treatments may be used without departing from the scope of the present invention, in one embodiment the visually contrasting surface treatments include a first color on at least a portion of an exterior surface or outer face 112 of the flap 70 and a second color on at least a portion of an exterior surface 114 of the pocket 64. Further, it may be desirable that one of the colors be a raw material color of the packaging material and the other color be printed on the packaging 62. For example, if the raw material color of the packaging 62 is white, a lower edge margin 116 and opposing side margins 118 of the flap 70 may be substantially free of printing such as background coloration and text, and a central portion of the flap may include printing of a contrasting color (e.g., blue). The margins 116, 118 are delineated by phantom lines in the drawings. Although the edge margins 116, 118 may have other widths without departing from the scope of the present invention, in one embodiment the edge margins have a width 120 less than about 15 millimeters. It may be desirable that the widths 120 of the edge margins be about 4 millimeters. In addition to omitting printing from the edge margins 116, 118 of the flap 70, it may be desirable that the side margins of the pocket 64 (delineated by phantom lines) be substantially free of printing, to prevent printing discoloration when the sides are heat sealed. Further, it may be desirable that the flap 70 and/or the pocket 64 include a tactile indicator (not shown) for distinguishing the edge 74 of the flap from the pocket to improve tactile identification of the edge of the flap. It is envisioned that the tactile indicator could be a textured portion (e.g., knurling) on an exterior surface of the flap 70 and/or the pocket 64.

Figure 6:
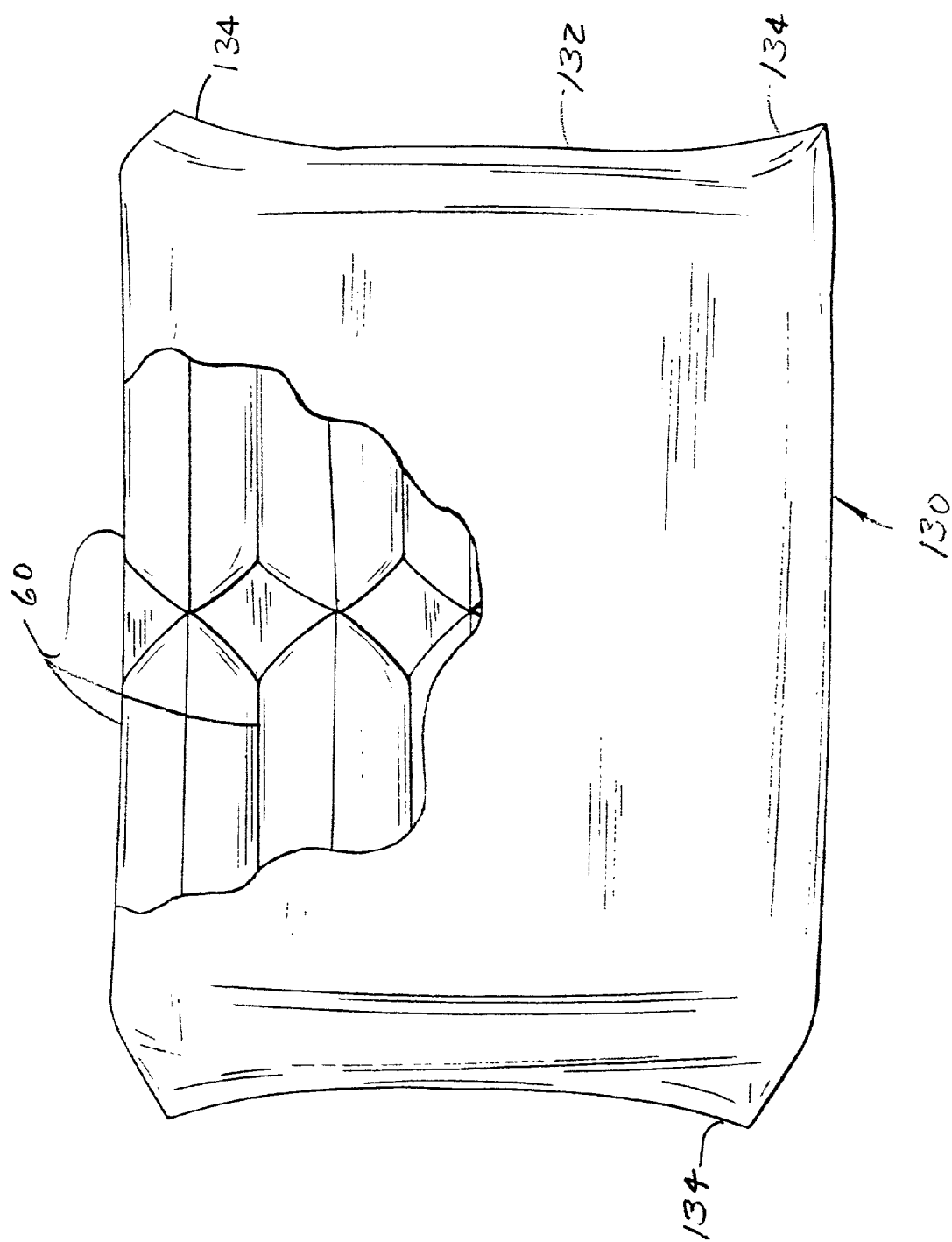
FIG. 6 is a front elevation of a master package of a first embodiment of the present invention with a portion broken away to show utility packages therein.

A master package is designated in its entirety by the numeral 130 in FIG. 6. The master package 130 includes a plurality of the utility packages 60 as described above. In addition, the master package 130 includes removable master packaging 132 surrounding the utility packages 60. The master packaging 132 has a hollow interior sized and shaped for receiving the utility packages. It is envisioned that the master packaging may have printing (not shown) on its exterior surface. It is further envisioned that the utility packages 60 may be arranged one or more stacks inside the master packaging 132. For example, the utility packages 60 may be arranged in two stacks as shown in FIG. 6 or arranged in one stack as shown in FIG. 7. Although the master package 130 may include different numbers of utility packages 60 without departing from the scope of the present invention, in the illustrated embodiments the master package includes less than about twelve utility packages. For example, the master package 130 may include about ten utility packages 60 as shown in FIG. 6 or about nine utility packages as shown in FIG. 7. Further, it may be desirable that one or more sides of the master packaging 132 include conventional gussets 134 to provide the packaging with flat sides. Although the master packaging 132 may be made of other materials without departing from the scope of the present invention, in one embodiment the master packaging is made from polyethylene sheet material having a thickness of about 45 microns using conventional packaging methods.

Figure 9:
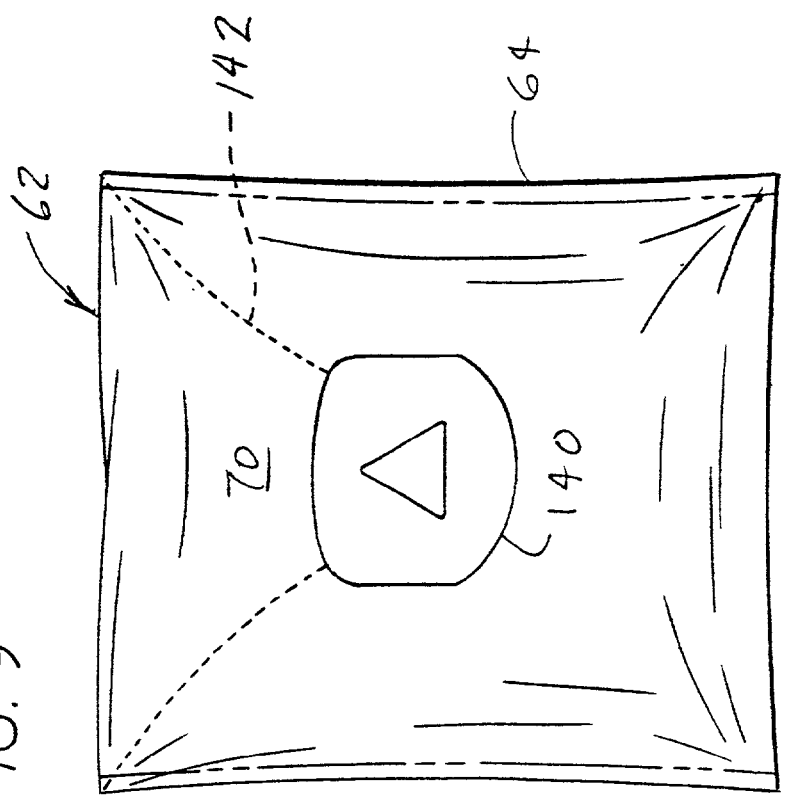
FIG. 9 is a front elevation of a utility package of a third embodiment of the present invention.
Figure 8:
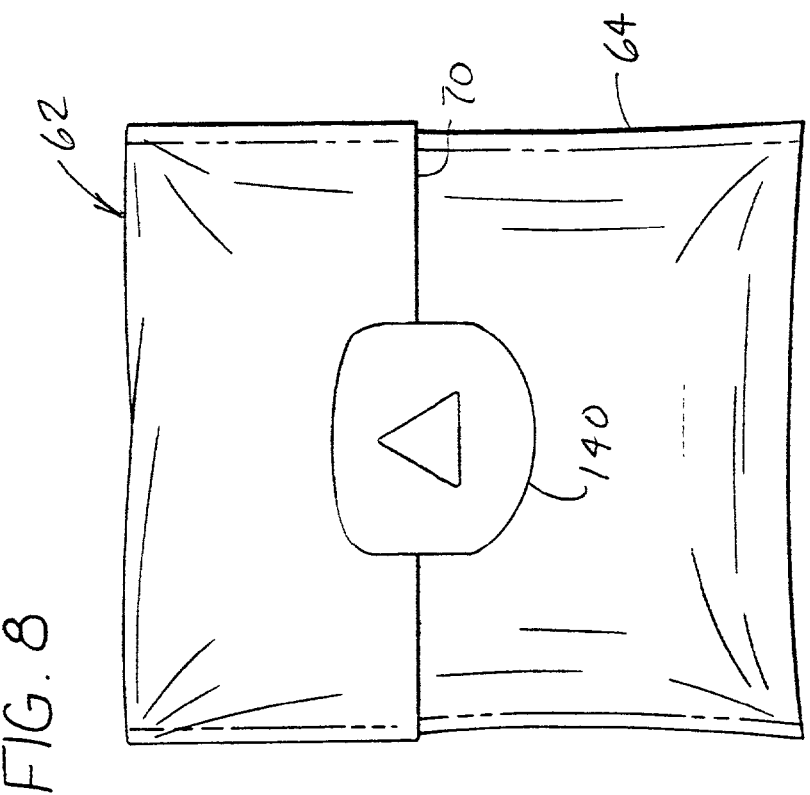
FIG. 8 is a front elevation of a utility package of a second embodiment of the present invention.

It is envisioned that the utility packages 60 may have alternative constructions without departing from the scope of the present invention. For instance, as illustrated in FIG. 8 a conventional adhesive tab closure 140 may be used to hold the flap 70 in its closed position against the pocket 64 of the packaging 62. Another embodiment shown in FIG. 9 is similar to that of FIG. 8 except that the flap 70 has a generally triangular configuration and is initially joined to the pocket 64 by frangible perforations 142.

Referring to FIGS. 10 and 11 of the drawings, an interlabial pad is designated in its entirety by the reference number 150. The pad 150, which is exemplary of interlabial pads that may be packaged in accordance with this invention, is generally of the type disclosed in the aforesaid U.S. Pat. Nos. 4,595,392 and 4,673,403, which are hereby incorporated by reference. In one embodiment, the pad 150 is generally oval and has lateral projections 152. As those skilled in the art will appreciate, the interlabial pad may have other shapes without departing from the scope of the present invention. Although the pad 150 of one embodiment comprises a lamination of a layer 154 of absorbent material on a fluid impervious layer 156 (e.g., plastic film), pads having other configurations including those without an impervious layer are also contemplated. As shown in FIGS. 12 and 13, in one embodiment the pad 150 is folded in half on its major axis as indicated at 158 and, as shown in FIGS. 14 and 15, is individually packaged in an elongate, generally flat sealed hygienic package 160 having a longitudinal seam 162 and end seals 164. In alternative embodiments, it is envisioned that the package 160 may not be sealed or may be omitted entirely. Further, it is envisioned that the pad 150 may be unfolded without departing from the scope of the present invention. Although the package 160 may be made of other materials without departing from the scope of the present invention, in one embodiment the package is made of heat-sealable plastic film and in another embodiment the package is made of paper. The seam 162 and seals 164 may be made by any conventional process such as heat sealing, mechanical sealing or adhesive bonding. Further, it is envisioned that the pad 150 may be sealed in the package 160 with a cardboard backing 165.

As illustrated in FIGS. 16 and 17, a package of a fourth embodiment of the present invention is designated in its entirety by the reference numeral 166. The package 166, carries a supply 168 of the interlabial pads 150 individually wrapped in their respective sealed hygienic packages 160 readily available for use when needed. The package 166 generally comprises a receptacle 170 (e.g., a pocket) having a mouth or opening 172 (see FIG. 19 particularly) through which a pad 150 in its sealed package 160 may be withdrawn for use when needed. The receptacle 170 has a reclosable flap 179 for closing the opening 172. The flap 174 may be closed after a pad 150 is withdrawn to retain the remaining pads in the receptacle 170 until needed.

The receptacle 170 comprises a bag having front and back walls 176 and 178 joined at the sides 180 and 182 and bottom 184 and free from each other at the top to define the opening 172. The flap 174 which is integral with the back wall 178 may be folded over the opening 172 so it overlies the front wall 176. The flap 174 is releasably adhered to the front wall 176 by an adhesive or mechanical closure 186. The receptacle 176 is formed from an elongate rectangular blank folded along fold 184 to form the front and back walls 176, 178, respectively. In one embodiment, the blank is a plastic film such as polyethylene film. In alternative embodiments, the blank is a non-woven material or a non-woven and film laminate. The fold 184 constitutes the bottom of the receptacle 170. The front and back walls 176, 178 are sealed together as by heat seals 180s and 182s at both sides, and are free from each other at the top to define the bag opening 172. The plastic film (e.g., polyethylene) from which the bag is made is generally opaque as by being pigmented (e.g., blue) to conceal the packaged pads in the bag. In one embodiment, the closure 186 is a spot 194 of pressure-sensitive adhesive such as two-sided tape for releasably adhering the flap 174. In an alternative embodiment (not shown), the closure 186 includes a stripe of pressure-sensitive adhesive extending from side to side along the receptacle 170. The packages 160 of pads 150 (e.g., from about three to about six in number) are aligned vertically so they extend from the opening 172 to the bottom 184 of the receptacle 170. In an alternative embodiment, it is envisioned that the pads 150 may be aligned horizontally from side to side in the receptacle 170. Although the receptacle 170 may have other dimensions without departing from the scope of the present invention, in one embodiment the receptacle has an overall width measured from side to side of about 10.8 cm and an overall height measured from the opening 172 to the bottom 184 of between about 9.5 cm and about 14.0 cm. Further, the flap 174 of this one embodiment has a width matching the width of the receptacle 170 and a height of about 5.1 cm. It is further envisioned that the package 166 of the fourth embodiment of the present invention may include various features described above with respect to the packages of the first, second and third embodiments.

Thus, the supply 168 of pads 150 is carried in a hygienic condition. Because the receptacle 170 (including the flap 174) is opaque, the contents are not visible and thus are carried in a discreet manner. A pad 150 is readily available for use in hygienic condition when needed by pulling the flap 184 back (to the open condition illustrated in FIGS. 18 and 19) to open the receptacle 170, withdrawing a sealed package 160, and tearing it open to access the pad 150 therein. The torn-open package 160 is discarded. The flap 174 may then be re-adhered to the front wall 176 of the receptacle 170 to re-close the bag by means of the closure 186.

FIGS. 20 and 21 illustrate a fifth embodiment of the package of the present invention, designated by 196 in its entirety. The package 196 of the fifth embodiment again comprises an opaque plastic receptacle 198 having front and back walls 200, 202, respectively, joined at the sides 204, 206 by heat-sealed side seams, having a fold 208 for the bottom and an opening 210. Instead of the flap 174 and closure 186, the receptacle 198 is provided with conventional press-fit members 212 and 214 (i.e., conventional interlockable plastic channels) extending across the front and back walls 200, 202 adjacent the opening 210. The receptacle 198 holds a plurality (e.g., three to six) packages 160 of pads 150. Although in the illustrated embodiment the packages 160 extend vertically from the bottom 208 to adjacent the opening 210 just below the press-fit members 212, 214, it is also envisioned that the packages may extend horizontally from side to side. The press-fit members 212, 214 are conventionally used on plastic bags and will not be described in further detail. Although the receptacle 198 may have other dimensions without departing from the scope of the present invention, in one embodiment the receptacle has an overall width measured from side to side of about 10.8 cm and an overall height measured from the opening 210 to the bottom 208 of between about 9.5 cm and about 14.0 cm.

FIGS. 22 and 23 illustrate a sixth embodiment of the package of the present invention, designated by 216 in its entirety. For the most part, the package 216 of the sixth embodiment is the same as the package 196 of the fifth embodiment except for the use of conventional slide fastener members 218 and 220 (instead of press-fit members 212 and 214) and a conventional slide fastener 222. Members 218, 220 and slide fastener 222 are such as conventionally used on plastic bags and will not be described in further detail. Although the receptacle of the package 216 of the sixth embodiment may have other dimensions without departing from the scope of the present invention, in one embodiment the receptacle has an overall width measured from side to side of between about 9.5 cm and about 14.0 cm and an overall height measured from the opening to the bottom of about 10.8 cm.

FIGS. 24–26 illustrate a seventh embodiment of the package of the present invention, designated by 230 in its entirety. The package 230 of the seventh embodiment is in the style of wallet and has two pockets 232 and 234, each having an opening 232m, 234m, facing the other opening. The package 230 may be folded in half with the openings 232m, 234m on the inside. Packages 160 of pads 150 are stocked in the pockets. The package 230 comprises an elongate rectangular outside wall 236 of the opaque plastic film and inside walls 238 and 240 of said film extending across the inside face 242 of the outside wall from one side of the outside wall to the other and inward from the ends of the outside wall. Each inside wall 238, 240 terminates short of the center of the outside wall 236 thereby forming the openings 232m, 234m of a pad-containing pocket.

In further detail, the receptacle 230 comprises an elongate rectangular blank of the opaque plastic film, portions of which are folded over as indicated at 244, 246 to form the inside walls 238, 240. The folds 244, 246 form the bottoms of the pockets 232, 234. The folded-over end portions forming the inside walls 238, 240 are heat-sealed at both sides as indicated at 248 and 250 to the portion of the blank between folds 244, 246 constituting the outside wall 236. The openings of the pockets 232, 234 lie on opposite sides of a fold line F at the center of the outside wall 236 on which the receptacle is foldable as illustrated in FIG. 26. The receptacle 230 may be held closed by a tab 252 heat-sealed to the outside wall 236 and having a spot (or stripe) 254 of pressure-sensitive adhesive thereon. Or, as shown in FIG. 27, the spot (or stripe) 254 may be applied to one of the inside walls, e.g., inside wall 240 to form a package of a eighth embodiment. Although the pockets 232, 234 of the packages 230 of the seventh and eighth embodiments may have other dimensions without departing from the scope of the present invention, in one embodiment the pockets have overall widths measured from side to side of between about 9.5 cm and about 14.0 cm and overall heights measured from the respective opening to the respective bottom of between about 6.3 cm and about 8.9 cm.

Although the interlabial pad packages are described above as containing interlabial pads, those skilled in the art will appreciate that the packages may include other feminine care products and associated supplies. For example, the packages may contain a supply of interlabial pads and a supply of tampons and/or panty liners. Examples of associated supplies which the packages may contain include wipes and/or tissues. Further, it is envisioned that the packages may include more than one size of interlabial pad without departing from the scope of the present invention.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A package comprising:
a plural number of individually wrapped absorbent feminine care articles; and
reclosable packaging comprising:
a middle portion and a back portion together at least in part forming a flexible pocket having a hollow interior receiving said plural number of absorbent feminine care articles;
the hollow interior of the pocket having a volume which is substantially filled by the plural number of individually wrapped feminine care articles so that the pocket conforms to the articles, said pocket being of single-piece construction;
an opening extending into the hollow interior of the pocket, said opening being sized and shaped for permitting at least one of said plural number of individually wrapped feminine care articles to be withdrawn from said hollow interior of the pocket;
a flap attached to the pocket and adapted for covering the opening to retain said plural number of individually wrapped feminine care articles in the hollow interior of the pocket, said flap being selectably moveable between an open position in which the opening is generally unobstructed by said flap to permit said article to be withdrawn through the opening and a closed position in which the flap covers the opening and at least a portion of an exterior area of the middle portion of the pocket to retain said plural number of articles in the pocket and to prevent said plural number of articles from passing through the opening; and
a reclosable adhesive closure comprising an adhesive material positioned on said flap for releasably securing the flap in its closed position on said exterior area of the middle portion of the pocket, the adhesive closure being spaced from a distal edge of the flap to permit a portion of the flap to be grasped and separated from the pocket without releasing the closure, said flap being releasably securable by said adhesive closure substantially anywhere on said exterior area of said middle portion of the pocket.

2. A package as set forth in claim 1 wherein the closure is positioned at least about 4 millimeters from the distal edge of the flap.

3. A package as set forth in claim 2 wherein the closure is positioned about 16 millimeters from the distal edge of the flap.

4. A package as set forth in claim 1 wherein said distal edge is substantially straight and said adhesive closure includes an elongate strip of adhesive material extending substantially parallel to the distal edge of the packaging flap.

5. A package as set forth in claim 4 wherein the elongate strip of adhesive material has a width of less than about 20 millimeters.

6. A package as set forth in claim 5 wherein the strip of adhesive material has a width of more than about 2 millimeters.

7. A package as set forth in claim 5 wherein the strip of adhesive material has a width of about 7 millimeters.

8. A package as set forth in claim 4 wherein the strip of adhesive material is substantially continuous and uninterrupted along its entire length.

9. A package as set forth in claim 4 wherein the flap is substantially rectangular.

10. A package as set forth in claim 1 wherein the adhesive closure extends substantially an entire width of the flap.

11. A package as set forth in claim 1 wherein the adhesive closure is a two sided tape.

12. A package as set forth in claim 1 wherein the adhesive closure is a hot melt adhesive.

13. A package as set forth in claim 1 wherein the flap has an inner face and an outer face, and the adhesive closure is positioned on said inner, face of the flap for releasably holding said flap in the closed position.

14. A package as set forth in claim 1 wherein the plurality of absorbent articles are arranged in a stack.

15. A package as set forth in claim 1 wherein the feminine care product comprises a panty liner.

16. A package as set forth in claim 1 wherein the feminine care product comprises an interlabial pad.

17. A package comprising:
a plural number of individually wrapped absorbent feminine care articles; and
reclosable packaging comprising:
a middle portion and a back portion together forming a flexible pocket having a hollow interior receiving said plural number of absorbent feminine care articles, the hollow interior of the pocket having a volume which is substantially filled by the plural number of individually wrapped feminine care articles so that the pocket conforms to the articles;
an opening extending into the hollow interior of the pocket, said opening being sized and shaped for permitting at least one of said plural number of individually wrapped feminine care articles to be withdrawn from said hollow interior of the pocket;
a flap attached to the pocket and adapted for covering the opening to retain said plural number of individually wrapped feminine care articles in the hollow interior of the pocket, said flap being selectably moveable between an open position in which the opening is generally unobstructed by said flap to permit said article to be withdrawn through the opening and a closed position in which the flap covers the opening and at least a portion of an exterior area of the middle portion of the pocket to retain said plural number of articles in the pocket and to prevent said plural number of articles from passing through the opening, the flap being everywhere free from flush alignment with the pocket in the closed position of said flap; and
a reclosable adhesive closure comprising an adhesive material positioned on said flap for releasably securing the flap in its closed position on said exterior area of the middle portion of the pocket, the adhesive closure being spaced from a distal edge of the flap to permit a portion of the flap to be grasped and separated from the pocket without releasing the closure, said flap being releasably securable by said adhesive closure substantially anywhere on said exterior area of said middle portion of the pocket.

18. A package comprising:
a plural number of individually wrapped absorbent feminine care articles; and
reclosable packaging comprising:
a flexible pocket comprising at least in part a first wall and having a hollow interior receiving said plural number of absorbent feminine care articles, the hollow interior of the pocket having a volume which is substantially filled by the plural number of individually wrapped feminine care articles so that the pocket conforms to the articles;

an opening extending into the hollow interior of the pocket, said opening being sized and shaped for permitting at least one of said plural number of individually wrapped feminine care articles to be withdrawn from said hollow interior of the pocket;

a flap attached to the pocket and adapted for covering the opening to retain said plural number of individually wrapped feminine care articles in the hollow interior of the pocket, said flap being selectably moveable between an open position in which the opening is generally unobstructed by said flap to permit said article to be withdrawn through the opening and a closed position in which the flap covers the opening and a first portion of the first wall of the pocket to retain said plural number of articles in the pocket and to prevent said plural number of articles from passing through the opening, a second portion of the first wall being uncovered by the flap in the closed position of the flap, the flap being free from flush alignment with said uncovered second portion of the first wall in the closed position of said flap; and a reclosable adhesive closure comprising an adhesive material positioned on said flap for releasably securing the flap in its closed position anywhere on said first portion of the first wall of the pocket, the adhesive closure being spaced from a distal edge of the flap to permit a portion of the flap to be grasped and separated from the pocket without releasing the closure.

19. A package comprising:

a plural number of individually wrapped absorbent feminine care articles; and reclosable packaging comprising:

a rectangular sheet having opposing side edges and opposite end edges;

a first fold extending between the side edges of the sheet to define a bottom of the packaging, the first fold separating a middle portion of the packaging from a back portion of the packaging, the middle and back portions of the packaging being sealingly joined along overlapping side edges to define a flexible pocket;

the pocket having a hollow interior for receiving said plural number of absorbent feminine care articles, the hollow interior of the pocket having a volume which is substantially filled by the plural number of individually wrapped feminine care articles so that the pocket conforms to the articles;

an opening extending into the hollow interior of the pocket, said opening being sized and shaped for permitting at least one of said plural number of individually wrapped feminine care articles to be withdrawn from said hollow interior of the pocket;

a second fold extending between the side edges of the sheet generally parallel to and above the first fold to define a top of the packaging, the second fold separating the back portion of the packaging from a front portion of the packaging, the front portion of the packaging defining a flap;

the flap being adapted for covering the opening to retain said plural number of individually wrapped feminine care articles in the hollow interior of the pocket, said flap being selectably moveable between an open position in which the opening is generally unobstructed by said flap to permit said article to be withdrawn through the opening and a closed position in which the flap covers the opening and a first portion of the middle portion of the pocket to retain said plural number of articles in the pocket and to prevent said plural number of articles from passing through the opening, a second portion of the middle portion being uncovered by the flap in the closed position of the flap, the flap being free from flush alignment with said uncovered second portion of the middle portion in the closed position of said flap; and a reclosable adhesive closure comprising an adhesive material positioned on said flap for releasably securing the flap in its closed position on the middle portion of the pocket, the adhesive closure being spaced from a distal edge of the flap to permit a portion of the flap to be grasped and separated from the pocket without releasing the closure, said flap being releasably securable by said adhesive closure substantially anywhere on said first portion of said middle portion of the pocket.

* * * * *